United States Patent [19]
Wettling et al.

[11] Patent Number: 5,886,209
[45] Date of Patent: *Mar. 23, 1999

[54] PREPARATION OF 2-(4-HYDROXYPHENOXY) PROPIONATES

[75] Inventors: Thomas Wettling, Limburgerhof; Manfred Dimmler, Dannstadt-Schauernheim; Bernd Hupfeld, Speyer; Jochem Henklemann, Mannheim, all of Germany

[73] Assignee: BASF Aktiengesellschaft, Ludwigshafen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 708,213

[22] Filed: Sep. 6, 1996

[30] Foreign Application Priority Data

Sep. 6, 1995 [DE] Germany ................ 195 32 815.9

[51] Int. Cl.⁶ ..................................... C07C 69/76
[52] U.S. Cl. ................................. 560/61; 560/67
[58] Field of Search ................ 560/103, 61, 67

[56] References Cited

U.S. PATENT DOCUMENTS 4,547,583  10/1985  Nestler .

OTHER PUBLICATIONS

Morrison and Boyd 3rd edition "Organic Chemistry" 1975 pp. 602–603.
Beilstein BRN 2720530–Record –#1 , 1981 Kuchan, Collect. Czech. Chem. Commun–1.

*Primary Examiner*—Gary Geist
*Assistant Examiner*—Jean F. Vollano
*Attorney, Agent, or Firm*—John H. Shurtleff

[57] ABSTRACT

A multi-stage catalytic process for preparing a 2-(4-hydroxyphenoxy)-propionate, especially methyl 2-(4-hydroxyphenoxy)-propionate, with a purity greater than 99% by esterifying the corresponding 2-(4-hydroxyphenoxy)-propionic acid with an excess amount of alcohol, e.g. methyl alcohol, in a series of at least 2 up to 10 sequential stages at temperatures of 20° to 150° C. and pressures of 0.05 to 5 bar in the presence of a distillable acid catalyst such as hydrochloric acid or hydrogen chloride. In a first esterification stage, unreacted alcohol is removed from the ester product in vacuo at temperatures of 30° to 100° C. together with other volatile components, including the acid catalyst. Without a separate purification of the resulting ester as the bottoms product of the first stage, the esterification step is repeated in at least one additional stage. The final ester product of this multi-stage process is characterized by a water content of less than 0.1%, a halide content of less than 100 ppm, an organic halogen content of less than 50 ppm and a content of all other contaminating compounds of less than 0.1%.

17 Claims, No Drawings

PREPARATION OF 2-(4-HYDROXYPHENOXY) PROPIONATES

The present invention relates to a process for the preparation of a 2-(4-hydroxyphenoxy)propionates, in particular methyl 2-(4-hydroxyphenoxy)propionate of high purity by the multi-stage reaction of the esterification mixture of the corresponding 2-(4-hydroxyphenoxy)propionic acids with an alcohol in the presence of distillable acid without the use of any additional purifying operation.

The preparation of carboxylates by the reaction of a carboxylic acid with an alcohol in the presence of catalytic amounts of an acid is described, eg, in Houben-Weyl, Methoden der Organischen Chemie, Vol. 5E, 1985, pp 658–663. Typical yields are in the range of 72–96%. In order to obtain esters of high purity it is therefore imperative to carry out additional purifying operations such as distillation.

Journal of Organic Chemistry 24, 261–262 (1959) and Journal of Organic Chemistry 28, 2898 (1963) reveal the preparation of methyl esters using stoichiometric amounts of acetone dimethyl acetate acting as water-binding agent. A drawback of this process is the non-quantitative conversion, the formation of stoichiometric amounts of acetone, and the elaborate preparation of acetone dimethyl acetate.

Chem. Ind. pp 1 568–1569 (1968) recommends the use of sulfuric acid as catalyst for the preparation of methyl carboxylates in Soxleth equipment. In this case either the catalyst remains in the product formed or alternatively the product must be isolated from the sulfuric acid, e.g. by distillation of the ester.

For separation of the water of reaction formed the use of a cosolvent, e.g. toluene, is recommended (Journal of Organic Chemistry 23, 108–110 (1958)). In this case the toluene is used as solvent for the phase separation of the remaining sulfuric acid. A drawback of this method is the use of large amounts of sulfuric acid and an additional solvent, which must either be purified and recycled or disposed of.

Furthermore considerable problems arise due to the presence, in the product, of traces of the acid catalyst or reaction products of carboxylic acid with the product. When large amounts of hydrochloric acid (or hydrogen chloride) are used as acid catalyst undesirable chlorinated reaction products of the alcohols and carboxylic acids used may be formed even under standard reaction conditions (Houben-Weyl, Methoden der Organischen Chemie, Vol. 5/3, pp 831–837 (1962)).

It is thus an object of the present invention to overcome the above drawbacks, in particular to provide a process for the production of hydroxyphenoxypropionates of high purity without further purification and thus with a reduction of purification losses.

Accordingly, we have found a novel and improved process for the preparation of 2-(4-hydroxyphenoxy) propionates of the general formula I

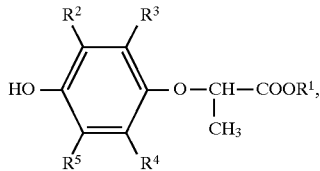

in which
 $R^1$ denotes $C_1$–$C_{18}$ alkyl, $C_2$–$C_8$ alkynyl, tetrahydrofurfuryl, or $C_3$–$C_{18}$ alkoxyalkyl and
 $R^2$, $R^3$, $R^4$, and $R^5$ denote hydrogen, $C_1$–$C_4$ alkyl, fluorine, chlorine, or bromine by the reaction of 2-(4-hydroxyphenoxy)propionic acids of the general formula II

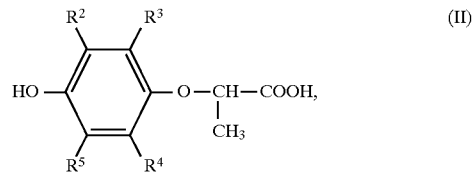

in which $R^2$, $R^3$, $R^4$, and $R^5$ have the meanings stated above, with alcohols of the general formula III $R^1$—OH (III) in which $R^1$ has the meanings stated above, wherein the esterification of 2-(hydroxyphenoxy)propionic acid II is carried out two to ten times at temperatures ranging from 20° to 150° C. and a pressure of from 0.05 to 5 bar with an alcohol III in the presence of distillable acid.

The process of the invention may be carried out as follows:

The reaction of the invention may be carried out either continuously or batchwise at temperatures ranging from 20° to 150° C., preferably from 40° to 130° C. and more preferably from 50° to 120° C. and a pressure of from 0.05 to 5 bar, preferably from 0.5 to 2 bar and more preferably standard pressure (atmospheric pressure) usually by admixing a distillable acid to a mixture of 2-(hydroxyphenoxy)-propionic acid II and an alcohol III (a fresh alcohol or one recovered from one of the reaction sequences) followed by removal of alcohol and optionally other volatile components in vacuo at temperatures ranging from 30° to 100° C. and preferably from 50° to 90° C. and a pressure of 15–720 mbar, preferably 20–700 mbar and more preferably 30–650 mbar, without purification of the bottoms. The bottoms are caused to react in accordance with the present invention without purification for another one to nine times (i.e. in all two to ten times), preferably one to four times (i.e. in all two to five times) and more preferably once or twice (i.e. in all two to three times) at temperatures ranging from 20° to 150° C., preferably from 40° to 130° C. and more preferably from 50° to 120° C. and a pressure of from 0.05 to 5 bar, preferably from 0.5 to 2 bar and more preferably standard pressure (atmospheric pressure) usually by admixing a distillable acid to a mixture of 2-(hydroxyphenoxy)propionic acid II and an alcohol III followed by removal of alcohol and optionally other volatile components in vacuo at temperatures ranging from 30° to 100° C. and preferably from 50° to 90° C. and a pressure of 15–720 mbar, preferably 20–700 mbar and more preferably 30–650 mbar, without purification of the bottoms.

The molar ratio of the alcohol III to 2-(hydroxyphenoxy) propionic acid II is usually 1:1 to 30:1, preferably 1.5:1 to 20:1 and more preferably 2:1 to 15:1.

The molar ratio of distillable acid to alcohol III is usually 0.0001:1 to 0.1:1, preferably 0.001:1 to 0.05:1 and more preferably 0.005:1 to 0.03:1.

Suitable distillable acids are hydrochloric acid, hydrobromic acid, hydrogen chloride, hydrogen bromide, and halogenated acetic acid derivatives such as trichloroacetic acid, trifluoroacetic acid, trifluoromethanesulfonic acid, and boron trifluoride, and also compounds which liberate such distillable acids in aqueous medium (e.g., methyl chloroformate-$H_2O$, methanol, $CO_2$, hydrogen chloride), preferably hydrochloric acid, hydrogen chloride, and boron trifluoride and more preferably hydrochloric acid and hydrogen chloride.

The process of the invention is suitable for the esterification of racemic 2-(4-hydroxyphenoxy)propionic acids, and for the chiralic enantiomers, preferably those having an enantiomer ratio of R:S of smaller than 5:95 and more preferably smaller than 2:98, or greater than 95:5 and more preferably greater than 98:2.

During esterification of the chiralic carboxylic acid the chirality in the resulting ester remains substantially intact (preferably ±5 and more preferably ±5).

In a particular embodiment the 2-(4-hydroxyphenoxy) propionic acid is dissolved in the corresponding alcohol and, for the first esterification stage, mixed with catalytic amounts of an acid and heated. There then commences the removal of the solvent in vacuo from the first esterification stage. The excess alcohol and the resulting water of reaction, or any water already present in the acid, are distilled off as quickly as possible and, when methanol is used as alcohol component, preferably under reduced pressure, in order to increase the water content of the distillate. At the same time, a large part of the previously added acid is also removed. The temperature of the molten product is adjusted such that the product is just still liquid and readily stirrable.

The second esterification stage then commences with the addition of fresh alcohol and a preferably reduced amount of acid. If two esterification stages suffice to attain the desired conversion, it is preferred to use an amount of alcohol comparable to that employed in the first stage. If three or more esterification stages are necessary to attain the desired degree of conversion, amount of alcohol used in the second and all of the following esterification stages except the last stage are advantageously distinctly reduced (e.g., by a third). The second and all of the following distillation phases are carried out in a manner analogous to that employed in the first stage. Following the last of the alcohol distillations required (in which case the alcohol distillate is kept for the first esterification stage of the following batch), the temperature of the reaction mixture lowered to such an extent that the melt remains just stirrable (preferably from 60° to 90° C.) and a reduced pressure is applied to the reaction vessel for the removal of traces of the acid used. To accelerate the removal of readily volatile impurities it is recommended to simultaneously pass in a stream of nitrogen into the reaction medium.

The 2-(4-hydroxyphenoxy)propionate prepared by the process of the invention is characterized, without any necessity for a purification stage, by a purity of >99%, a water content of <0.1%, a halide content of <100 ppm, an organic halogen content of <50 ppm and a content of other individual contaminating compounds, in particular hydroxyphenoxypropionic acid oligomers, of <0.1%.

The product can then be used directly, without further purification, for subsequent reactions, or be subjected to ancillary processing (eg flaked) for storage and transport.

The substituents $R^1$, $R^2$, $R^3$, $R^4$, and $R^5$ in the compounds I, II, and III have the following meanings:

$R^1$
- $C_1$–$C_{18}$ alkyl, preferably $C_1$–$C_{12}$ alkyl and more preferably $C_1$–$C_8$ alkyl, such as methyl, ethyl, n-propyl, isopropyl, n-butyl, isobutyl, tert-butyl, ethylhexyl,
- $C_3$–$C_{18}$ alkoxyalkyl, preferably $C_3$–$C_{12}$ alkoxyalkyl and more preferably $C_3$–$C_8$ alkoxyalkyl such as methoxyethyl and ethoxyethyl,
- $C_2$–$C_8$ alkynyl, preferably propargyl,
- tetrahydrofurfuryl, $R^2$, $R^3$, $R^4$, and $R^5$
- hydrogen,
- $C_1$–$C_4$ alkyl such as methyl, ethyl, n-propyl, isopropyl, n-butyl, isobutyl, and tert-butyl, preferably methyl and ethyl and more preferably methyl, fluorine, chlorine or bromine.

In particular those compound I, II and III are preferred in which $R^1$ stands for methyl and $R^2$, $R^3$, $R^4$, and $R^5$ all stand for hydrogen.

The 2-(4-hydroxyphenoxy)propionate I are suitable for use as intermediates in the synthesis of plant protectants and medicines.

EXAMPLES

Example 1

To 191 g (1 mol) of 2-(4-hydroxyphenoxy)propionic acid, moist (5% $H_2O$ content) and 160 g (5 mol) of methanol there were added 2 g (0.02 mol) of 36% strength hydrochloric acid and the mixture was refluxed for 2 h. Following removal of the solvent in vacuo (600–30 mbar/80° C. base temperature) there were obtained 194 g of methyl hydroxyphenoxypropionate (ester content: 95,9%, chloride value: 2100 ppm ).

The product thus obtained (chloride value: 2100 ppm) was again refluxed with 160 g (5 mol) of methanol and 2 g (0.02 mol) of 36% strength hydrochloric acid over a period of 1.5 h. The product was worked up in a manner similar to that described above to give 196 g of methyl hydroxyphenoxypropionate (ester content: 99,4%, chloride value: 190 ppm ).

The product thus obtained (chloride value: 190 ppm) was again refluxed with 160 g (5 mol) of methanol and 2 g (0.02 mol) of 36% strength hydrochloric acid over a period of 1 h. The product was worked up in a manner similar to that described above to give 196 g (100% ) [content: 99,7%] of methyl hydroxyphenoxypropionate (chloride value: 29 ppm; organic chlorine: <10 ppm, other impurities: <0,1%, [hydroxyphenoxypropionic acid not detectable]).

EXAMPLE 2

In a manner similar to that described in Example 1 191 g (1 mol) of R-2-(4-hydroxyphenoxy)propionic acid, moist (5% $H_2O$ content) and having an R:S-ratio of 99.3:0.7 was caused to react. Following three esterification stages there were obtained 196 g (100% ) [content: 99,7% of methyl R-2-(4-hydroxyphenoxy)propionate having an enantiomer ratio R:S of 99.4:0.6 (chloride value: 29 ppm; organic chlorine: <10 ppm, other impurities: <0,1%, [R-hydroxyphenoxypropionic acid impurities not detectable]).

EXAMPLE 3

Into a mixture of 191 g (1 mol) of 2-(4-hydroxyphenoxy) propionic acid, moist (5% of $H_2O$ content), and 160 g (5 mol) of methanol there was blown in 0.73 g (0.02 mol) of hydrogen chloride and the mixture was caused to react and purified in a manner similar to that described in example 1. There were obtained 196 g (100%) [content: 99,7%] of methyl 2-(4-hydroxyphenoxy)propionate (chloride value: 34 ppm; organic chlorine: <10 ppm, other impurities: <0,1%, [hydroxyphenoxypropionic acid not detectable]).

EXAMPLE 4

In a manner similar to that described in example 10.5 g (0.013 mol) of hydrogen chloride were blown into a mixture of 182 g (1 mol) of R-2-(4-hydroxyphenoxy)propionic acid (enantiomer ratio R:S of 99.2:0.8) and 160 g (5 mol) of methanol and the mixture was refluxed over a period of 4 h. Following removal of the solvent in vacuo another 160 g of methanol without further hydrogen chloride were added and the mixture was refluxed over a period of 4 h and the solvent removed in vacuo. Subsequently nitrogen was passed through the reaction mixture under a reduced pressure of 15 mbar over a period of 5 h. There were obtained 196 g (100%) [content: 99,6%] of methyl R-2-(4-hydroxyphenoxy)propionate having an enantiomer ratio R:S of 99.2:0.8 (chloride value: 33 ppm; organic chlorine not detectable, other impurities: <0,1%, [R-hydroxyphenoxypropionic acid impurities not detectable]).

EXAMPLE 5

Example 4 was repeated except that 1 g (0.012 mol) of hydrogen bromide was blown in the first esterification stage. There were obtained 196 g (100% ) [content: 99,4%] of methyl 2-(4-hydroxyphenoxy)propionate (0.3% of hydroxyphenoxypropionic acid).

EXAMPLE 6

Operating in a manner similar to that described in Example 1 149 g of methanol coming from a distillate of the third esterification stage of Example 1 were used in the first esterification stage. There were obtained 1 96 g (100%) [content: 99,7%] of methyl 2-(4-hydroxyphenoxy) propionate (0.1% of hydroxyphenoxypropionic acid).

EXAMPLE 7

193 g (1 mol) of R-2-(4-hydroxyphenoxy)propionic acid, moist (6% $H_2O$ content), and 160 g of recycled methanol were refluxed with 1,5 g of a 36% strength hydrochloric acid over a period of 2 h. Following removal of the solvent in vacuo (700–20 mbar/90° C. base temperature) 130 g of fresh methanol metered were metered in at 70° C. and 0.3 g (0.008 mol) of hydrogen chloride was blown in, the mixture then being refluxed over a period of 2 h and the solvent removed in vacuo as above. Subsequently 160 g of fresh methanol were metered in at 70° C. and the mixture was refluxed over a period of 4 h and the solvent removed in vacuo as above. Nitrogen was then passed through the reaction mixture under reduced pressure (ca 500 mbar). There were obtained 196 g (100% ) [content: 99,7%] of methyl R-2-(4-hydroxyphenoxy)propionate having an enantiomer ratio R:S of 99.5:0.5 (chloride value: 37 ppm; organic chlorine not detectable, 0.1% of R-hydroxyphenoxypropionic acid chlorine).

EXAMPLE 8–12

Methyl R-2-(4-hydroxyphenoxy)propionate was prepared in all five batches (Examples 8–12) in a manner similar to that described in Example 6 and in each case the distillate recovered from the third distillation stage of the previous batch was used for the first esterification stage of the following batch. The results are in Table 1.

TABLE 1

| Example No. | Methyl Hydroxyphenoxypropionate [content in %] | Hydroxyphenoxypropionic acid [content in %] | Chloride [content in ppm] |
| --- | --- | --- | --- |
| 8 | 99.6 | 0.1 | 27 |
| 9 | 99.7 | 0.1 | 41 |
| 10 | 99.7 | 0.1 | 36 |
| 11 | 99.6 | 0.1 | 33 |
| 12 | 99.7 | 0.1 | 35 | in no case could organic chlorine be detected (<10 ppm). Other impurities, in particular oligomers of hydroxyphenoxypropionic acid were under 0.1% (for each individual component and <0,3% in all).

EXAMPLES 13–16

To 365 g (2 mol) of R-2-(4-hydroxyphenoxy)propionic acid and 300 g of an alcohol specified in Table 2 below there were added 3 g of hydrochloric acid and the mixture was refluxed over a period of 1 h and the excess alcohol was removed by distillation under standard pressure conditions. Subsequently, 300 g of the same alcohol were added and 0.7 g of hydrogen chloride was blown in and the mixture refluxed over a period of 2 h. The solvent was then removed in vacuo (65° C./20 mbar) and nitrogen was passed through the bottom of the distilling apparatus over a period of 2 h. The results are listed in Table 2.

TABLE 2

| Example No. | Alcohol | . . . R-hydroxyphenoxypropionate | Content [%] |
| --- | --- | --- | --- |
| 13 | ethanol | ethyl | 99.4 |
| 14 | n-butanol | n-butyl | 99.5 |
| 15 | isobutanol | isobutyl | 99.5 |
| 16 | ethoxyethanol | ethoxyethyl | 99.4 |

We claim:

1. A catalytic process for the preparation of a 2-(4-hydroxyphenoxy)-propionate of the formula I

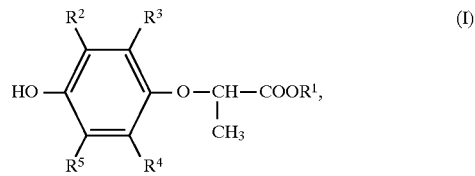

in which

R$^1$ is $C_1$–$C_{18}$-alkyl, $C_2$–$C_8$-alkynyl, tetrahydryofurfuryl or $C_2$–$C_{18}$-alkoxyalkyl, and R$^2$, R$^3$, R$^4$ and R$^5$ is hydrogen, $C_1$–$C_4$-alkyl, fluorine, chlorine or bromine, which comprises:

esterifying a 2-(4-hydroxyphenoxy)-propionic acid of the formula II

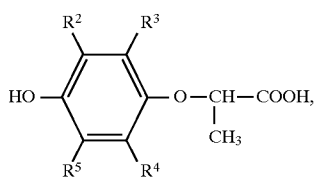

in which $R^2$, $R^3$, $R^4$ and $R^5$ have the meanings stated above, with an excess of an alcohol of the formula III $$R^1-OH \qquad (III),$$

in which $R^1$ has the meanings stated above, in a series of at least 2 up to 10 sequential stages at a temperature of from 20° to 150° C. and a pressure of from 0.05 to 5 bar in the presence of a distillable acid catalyst, removing unreacted alcohol III together with other volatile components in vacuo at a temperature of from 30° to 100° C. from the ester product of a first esterification stage and, without purification of the bottoms product, thereafter repeating at least the esterification step in at least one additional stage.

2. A process as claimed in claim 1, wherein the 2-(4-hydroxyphenoxy)propionic acid II is caused to react with an alcohol III two to five times.

3. A process as claimed in claim 1, wherein the molar ratio of alcohol III used to the 2-(4-hydroxyphenoxy)propionic acid II used is 1:1 to 30:1.

4. A process as claimed in claim 1, wherein the molar ratio of the distillable acid used to the alcohol III used is 0.0001:1 to 0.1:1.

5. A process as claimed in claim 1, wherein the substituent $R^1$ denotes methyl, ethyl, n-propyl, isopropyl, n-butyl, isobutyl, tert-butyl, ethylhexyl, methoxy- ethyl, propargyl, tetrahydrofurfuryl, or ethoxyethyl.

6. A process as claimed in claim 1, wherein the substituent $R^1$ denotes methyl.

7. A process as claimed in claim 1, wherein the substituents $R^2$, $R^3$, $R^4$, and $R^5$ denote hydrogen.

8. A process as claimed in claim 1, wherein the 2-(4-hydroxyphenoxy)-propionic acid II used has an enantiomer ratio R:S of smaller then 5:95 or greater than 95:5.

9. A process as claimed in claim 1, wherein the distillable acid used is hydrochloric acid or hydrogen chloride.

10. A process as claimed in claim 1, wherein the molar ratio of said distillable acid catalyst to the alcohol III during the esterification reaction is from about 0.001:1 to 0.1:1 in each stage of the reaction.

11. A process as claimed in claim 1, wherein the molar ratio of said distillable acid catalyst to the alcohol III during the esterification reaction is from about 0.005:1 to 0.03:1 in each stage of the reaction.

12. A process as claimed in claim 1, wherein the molar ratio of the alcohol III to the 2-(4-hydroxyphenoxy)-propionic acid II during the esterification reaction is from about 2:1 to 15:1 in each stage of the reaction.

13. A process as claimed in claim 12, wherein the reaction is carried out in a series of from 2 to 5 stages by using the bottoms product from each prior stage in the next succeeding stage.

14. A process as claimed in claim 12, wherein the reaction is carried out in a series of from 2 to 3 stages by using the bottoms product from the first stage in the second stage and then, optionally, the bottoms product from the second stage in the third and final stage.

15. A process as claimed in claim 12, wherein the temperature of the reaction mixture in the last stage is lowered to such an extent that bottoms product as a melt still remains stirrable while reducing the temperature and applying a reduced pressure sufficient to remove traces of the distillable acid.

16. A process as claimed in claim 12, wherein the removal of readily volatile impurities in the product is accelerated by simultaneously passing a stream of nitrogen under a reduced pressure through the final reaction mixture obtained as the bottoms product in the last stage.

17. The ester product, as obtained from the final stage of the process according to claim 12, which has a purity of >99%, a water content of <0.1%, an organic halogen content of <50 ppm and a content of other individual contaminating compounds, including hydroxyphenoxypropionic acid oligomers, of <0.1%.

* * * * *

UNITED STATES PATENT AND TRADEMARK OFFICE
CERTIFICATE OF CORRECTION

PATENT NO. : 5,886,209
DATED : March 23, 1999
INVENTOR(S) : Thomas Wettling, Manfred Dimmler, Bernd Hupfeld and Jochem Henkelmann It is certified that error appears in the above-identified patent and that said Letters Patent is hereby corrected as shown below:

On the title page, under "[75] Inventors:", correct the fourth inventor's name to --Henkelmann--.

In Claims 13, 14, 15, 16 and 17, line 1 of each: after "claim", cancel "12" and substitute --1--.

Signed and Sealed this

Twenty-fifth Day of January, 2000

Attest:

Attesting Officer

*Acting Commissioner of Patents and Trademarks*